United States Patent
Horn et al.

(10) Patent No.: US 9,346,771 B2
(45) Date of Patent: May 24, 2016

(54) PURIFICATION METHOD

(71) Applicant: GE Healthcare Limited, Buckinghamshire (GB)

(72) Inventors: Eric Horn, Buckinghamshire (GB); Steven Fairway, Oslo (NO); Dimitrios Mantzilas, Oslo (NO); Nigel Powell, Buckinghamshire (GB)

(73) Assignee: GE HEALTHCARE LIMITED, Amersham, Buckinghamshire (GB)

( * ) Notice: Subject to any disclaimer, the term of this patent is extended or adjusted under 35 U.S.C. 154(b) by 0 days.

(21) Appl. No.: 14/619,871

(22) Filed: Feb. 11, 2015

(65) Prior Publication Data
US 2015/0259307 A1    Sep. 17, 2015

Related U.S. Application Data

(62) Division of application No. 13/517,276, filed as application No. PCT/US2010/051891 on Oct. 8, 2010, now Pat. No. 8,969,580.

(60) Provisional application No. 61/315,507, filed on Mar. 19, 2010, provisional application No. 61/285,239, filed on Dec. 10, 2009, provisional application No. 61/249,656, filed on Oct. 8, 2009.

(51) Int. Cl.
*C07D 277/66* (2006.01)
*C07B 59/00* (2006.01)
*B01D 15/26* (2006.01)
*A61K 51/04* (2006.01)
*C07B 63/00* (2006.01)

(52) U.S. Cl.
CPC .......... *C07D 277/66* (2013.01); *A61K 51/0402* (2013.01); *B01D 15/26* (2013.01); *C07B 59/002* (2013.01); *C07B 63/00* (2013.01); *C07B 2200/05* (2013.01)

(58) Field of Classification Search
None
See application file for complete search history.

(56) References Cited

U.S. PATENT DOCUMENTS

2011/0008254 A1*  1/2011  Roed .................... A61K 9/0019
                                                         424/1.89

FOREIGN PATENT DOCUMENTS

WO    2009/027452    3/2009

OTHER PUBLICATIONS

PCT/US2010/051891 ISRWO Apr. 28, 2011, 10 pages.

* cited by examiner

*Primary Examiner* — Rebecca Anderson
*Assistant Examiner* — Po-Chih Chen
(74) *Attorney, Agent, or Firm* — Wood IP LLC

(57) ABSTRACT

A diagnostic imaging agent useful for positron emission tomography (PET) imaging as well as to improved hardware for producing such imaging agents is described. Flutemetamol ($^{18}$F) Injection for the imaging of β-amyloid plaques in the brain and methods and devices for preparing same are described including the automated synthesis and purification of [$^{18}$F]flutemetamol by means of solid phase extraction (SPE).

3 Claims, 11 Drawing Sheets

Key: EOS = end of synthesis

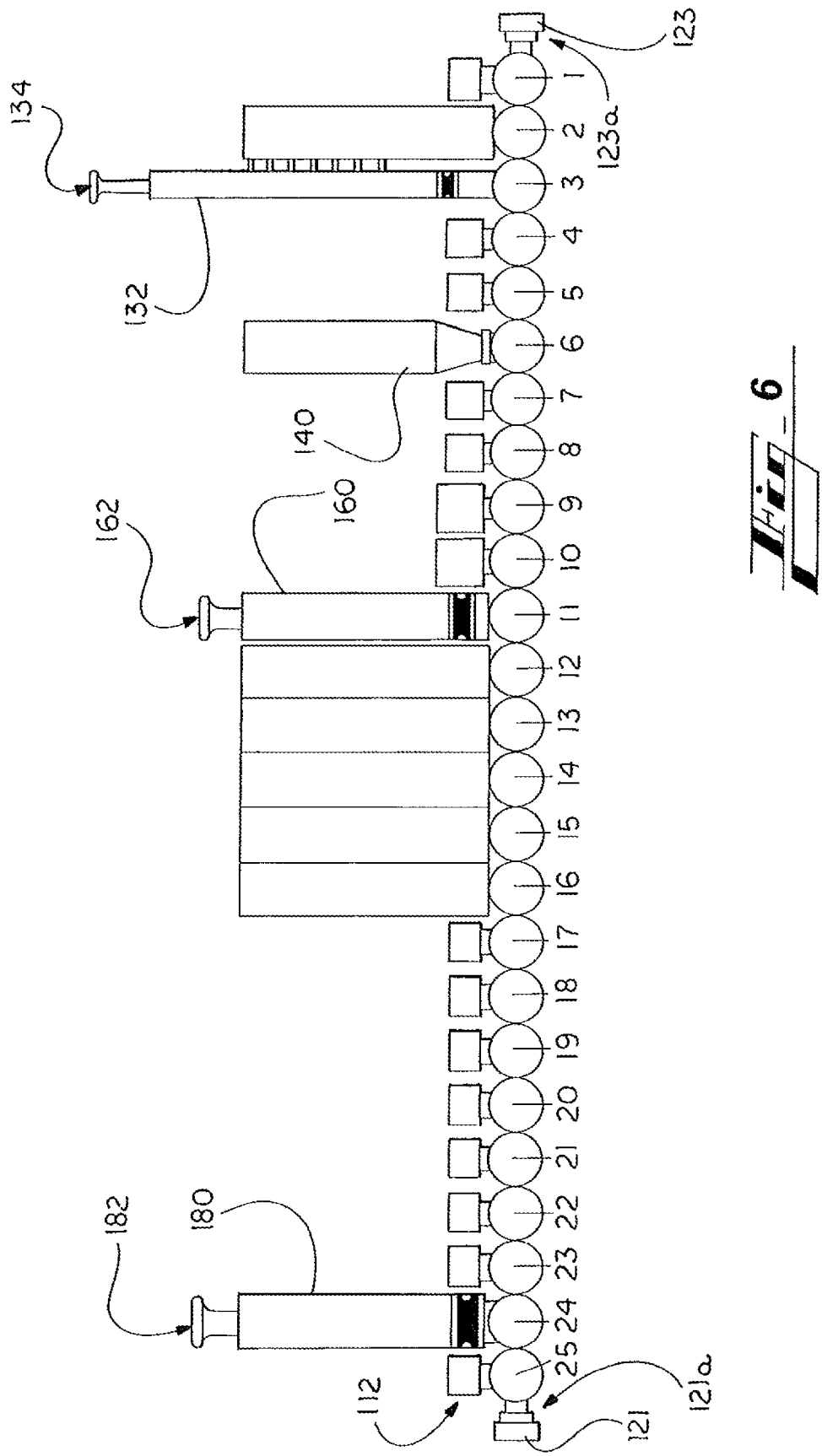

| RAW MATERIAL | FUNCTION |
|---|---|
| SOLUTION OF [$^{18}$F]FLUORIDE IN H$_2$[$^{18}$O] TARGET WATER | INCOMING SUPPLY OF [$^{18}$F]FLUORIDE TO FASTLAB |
| SOLUTION OF TETRABUTYLAMMONIUM BICARBONATE IN 80% ACETONITRILE:20% WATER (V/V) | ELUTION OF [$^{18}$F]FLUORIDE FROM QMA AND PHASE TRANSFER CATALYST |
| SOLUTION OF AH111907 (6-ETHOXYMETHOXY-2-(4'-(N-FORMYL-N-METHYL)AMINO-3'-NITRO)PHENYLBENZOTHIAZOLE) IN DMSO | FINAL INTERMEDIATE |
| SOLUTION OF SODIUM METHOXIDE IN METHANOL | CONVERSION OF UNLABELLED PRECURSOR |
| AQUEOUS SOLUTION OF HYDROCHLORIC ACID | DEPROTECTION OF RADIOLABELLED INTERMEDIATE |
| FASTLAB WATER BAG | MULTI-PURPOSE (INCLUDING DILUTION AND CASSETTE RINSING) |
| ETHANOL | ELUTION OF DRUG SUBSTANCE FROM C30 CARTRIDGES |
| ACETONITRILE / WATER | WASHING OF IMPURITIES FROM C30 CARTRIDGE |
| ACETONITRILE | CONDITIONING OF CARTRIDGES, ELUTION OF FLUTEMETAMOL FROM C30 CARTRIDGE |
| PRODUCT COLLECTION VIAL | FORMULATION AND SOLUBILISATION OF DRUG SUBSTANCE |
| WATERS QMA LIGHT CARBONATE | FLUORIDE RECOVERY FROM [$^{18}$O] ENRICHED WATER |
| C30 SPE CARTRIDGE | PRIMARY PURIFICATION OF CRUDE PRODUCT, SOLVENT EXCHANGE |
| VARIAN BOND ELUT JR-NH$_2$ CARTRIDGE | SECONDARY PURIFICATION OF DRUG SUBSTANCE |

FIG. 7

| MANIFOLD POSITION | CASSETTE COMPONENT |
|---|---|
| N/A | CASSETTE MANIFOLD |
| 1 | SILICONE TUBING (14 CM) TO TARGET RECOVERY VESSEL |
| 2 | TETRABUTYLAMMONIUM BICARBONATE ELUENT VIAL |
| 3 | 1 ML SYRINGE (PART OF MANIFOLD) |
| 4 | QMA CARTRIDGE WITH SILICONE TUBING (14 CM) TO POSITION 5 |
| 5 | SILICONE TUBING (14 CM) TO QMA CARTRIDGE AT POSITION 4 |
| 6 | FLUORIDE INLET RESERVOIR (PART OF MANIFOLD) |
| 7 | SILICONE TUBING (14 CM) TO REACTOR VESSEL LEFT HAND SIDE |
| 8 | SILICONE TUBING (14 CM) WITH YELLOW MARKINGS TO REACTOR VESSEL CENTRAL PORT |
| 9 | SILICONE TUBING (42 CM) WITH RED MARKINGS TO 40% MECN:60% WATER (V/V) VIAL |
| 10 | SILICONE TUBING (42 CM) WITH BLUE MARKINGS TO 100% MECN VIAL |
| 11 | 5 ML SYRINGE (PART OF MANIFOLD) |
| 12 | AH111907 (6-ETHOXYMETHOXY-2-(4'-(N-FORMYL-N-METHYL)AMINO-3'-NITRO)PHENYLBENZOTHIAZOLE) VIAL |
| 13 | HYDROCHLORIC ACID VIAL |
| 14 | SODIUM METHOXIDE VIAL |
| 15 | WATER BAG SPIKE |
| 16 | ETHANOL VIAL |
| 17 | SILICONE TUBING (14 CM) TO C30 CARTRIDGE AT POSITION 18 |
| 18 | C30 CARTRIDGE WITH SILICONE TUBING (14 CM) TO POSITION 17 |
| 19 | TYGON TUBING (50 CM) TO PRODUCT COLLECTION VIAL |
| 20 | SILICONE TUBING (14 CM) TO AMINO CARTRIDGE AT POSITION 21 |
| 21 | AMINO CARTRIDGE WITH SILICONE TUBING (14 CM) TO POSITION 20 |
| 22 | C30 CARTRIDGE WITH TYGON TUBING (8 CM) TO POSITION 23 |
| 23 | TYGON TUBING (8 CM) TO C30 CARTRIDGE AT POSITION 22 |
| 24 | 5 ML SYRINGE (PART OF MANIFOLD) |
| 25 | SILICONE TUBING (42 CM) TO REACTOR VESSEL RIGHT HAND SIDE |

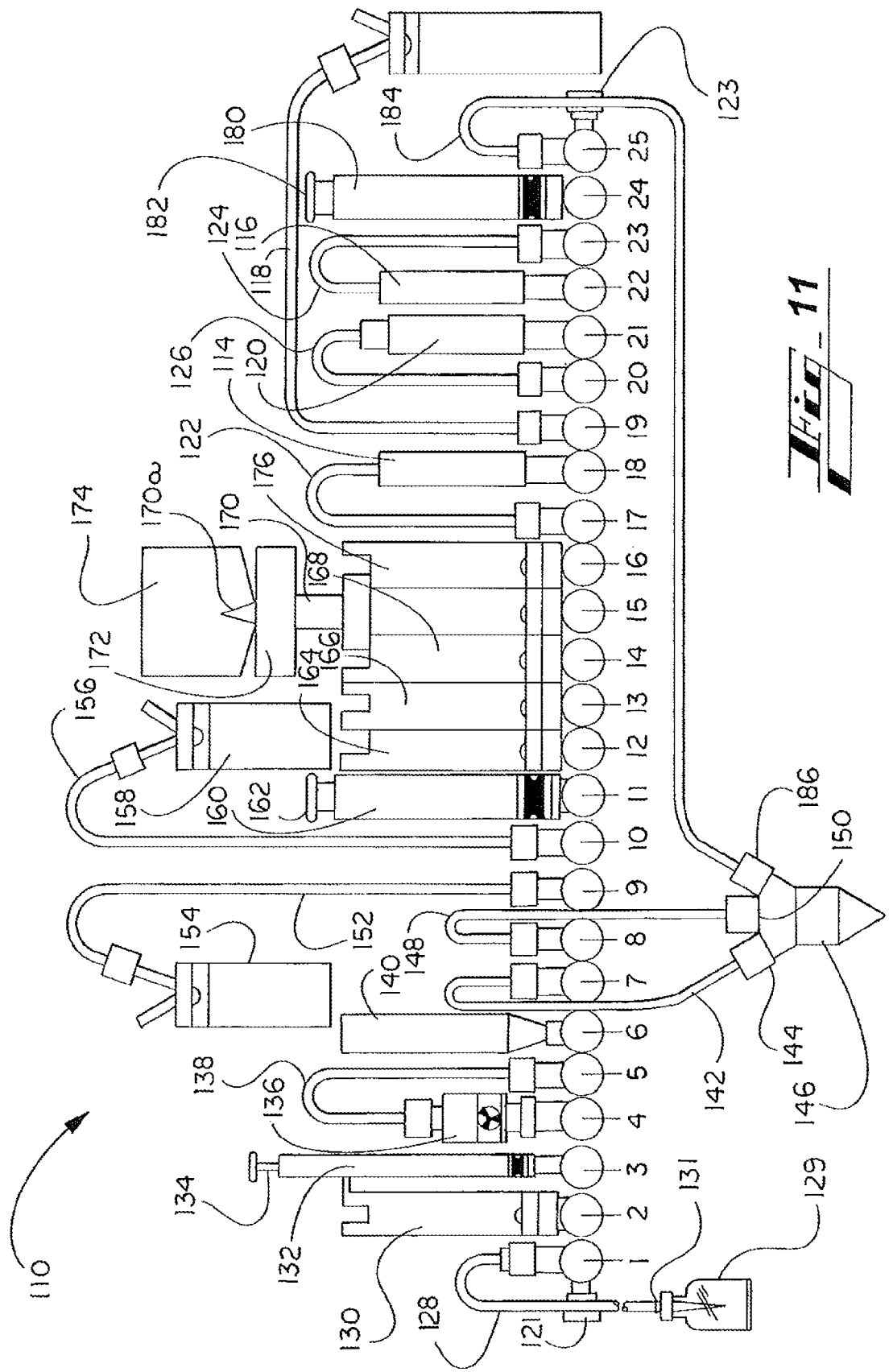

PURIFICATION METHOD

CROSS REFERENCE TO RELATED APPLICATIONS

This application is a divisional application of U.S. application Ser. No. 13/517,276, filed on Jun. 20, 2012, now allowed, which is a filing under 35 U.S.C. 371 of international application number PCT/US2010/051891, file Oct. 8, 2010, which claims priority to application No. 61/249,656 filed Oct. 8, 2009, 61/285,239 filed Dec. 10, 2009 and 61/315,507 filed Mar. 19, 2010, the entire disclosure of each of which is hereby incorporated by reference.

FIELD OF THE INVENTION

The present invention relates to a diagnostic imaging agent useful for positron emission tomography (PET) imaging as well as to improved hardware for producing such imaging agents. More specifically, the present invention is directed to method of purifying crude [$^{18}$F]flutemetamol which in turn can then be formulated into Flutemetamol [$^{18}$F] Injection for the imaging of β-amyloid plaques in the brain and methods and devices for preparing same. More specifically, the present invention is directed to the automated synthesis and purification of [$^{18}$F]flutemetamol by means of solid phase extraction (SPE).

BACKGROUND OF THE INVENTION

Flutemetamol [$^{18}$F] Injection is a diagnostic positron emission tomography (PET) agent for the imaging of β-amyloid plaques in the brain. The synthesis of the agent can be performed using automated synthesis platforms with or without using specially-tailored cassettes. For example, the synthesis can be performed using either the TRACERlab FX F-N platform or the FASTlab™ platform, commercially available from GE Healthcare a division of General Electric Company in conjunction with auxiliary preparative high pressure liquid chromatography equipment. After synthesis, the bulk agent is transferred to high pressure liquid chromatography (HPLC) equipment to separate the physico-chemically similar compounds [$^{18}$F]flutemetamol from its deprotected precursor, AH111832 (6-hydroxy-2-(4'-(N-methyl)amino-3'-nitro)phenylbenzothiazole) and hence obtain purified [$^{18}$F]flutemetamol.

However there still exists a need in the art for alternative purification methods for the preparation of [$^{18}$F]flutemetamol. The invention as described below answers such a need. Specifically, Applicants have now found a process that eliminates the use of preparative HPLC equipment.

SUMMARY OF THE INVENTION

As [$^{18}$F]flutemetamol and its deprotected precursor, AH111832 (6-hydroxy-2-(4'-(N-methyl)amino-3'-nitro)phenylbenzothiazole) are physico-chemically very similar, preparative HPLC is required to separate them. However, Applicants have now found that it is possible to replace the preparative HPLC equipment in previous purification processes with low cost, single-use solid phase extraction (SPE) cartridges for purification of [$^{18}$F]flutemetamol.

Accordingly, the present invention provides a purification process comprising the following steps:

(a) passing a diluted crude product reaction mixture comprising flutemetamol through a first reverse phase SPE cartridge;

(b) washing said first reverse phase SPE cartridge with a water/acetonitrile, tetrahydrofuran (THF)/water, methanol (MeOH)/water or isopropanol/water mixture; preferably, a water/acetonitrile mixture;

(c) rinsing said first reverse phase SPE cartridge with water once step (b) is completed;

(d) eluting said first reverse phase SPE cartridge with acetonitrile or tetrahydrofuran; preferably, acetonitrile;

(e) directly passing the mixture from said eluting step (d) through a normal phase SPE cartridge to give an acetonitrile or tetrahydrofuran solution; preferably, an acetonitrile solution, comprising purified flutemetamol;

(f) diluting said acetonitrile or tetrahydrofuran solution; preferably, an acetonitrile solution, comprising purified flutemetamol, with water to form a diluted water/acetonitrile or a diluted water/tetrahydrofuran solution; preferably, a diluted water/acetonitrile solution, comprising purified flutemetamol, wherein said water/acetonitrile solution contains about 40-70% (v/v) water; preferably at least about 40% (v/v) water; more preferably at least about 50% (v/v) water;

(g) passing the diluted water/acetonitrile or diluted water/tetrahydrofuran solution; preferably, diluted water/acetonitrile solution, comprising purified flutemetamol of step (f) through a second reverse phase SPE cartridge and trapping the flutemetamol on said cartridge second reverse phase SPE cartridge;

(h) rinsing said second reverse phase SPE cartridge with water; and (i) eluting the trapped purified flutemetamol from second reverse phase SPE cartridge with an injectable organic solvent; preferably, ethanol or DMSO; preferably with ethanol.

According to the invention, the purified flutemetamol can be collected after step (i).

The present invention also provides a purification process of the present invention, wherein the process is automated.

The present invention also provides a cassette on which a purification process of the present invention can be performed.

BRIEF DESCRIPTION OF THE FIGURES

FIG. 6 shows the numbering of each position of the cassette manifold of the present invention.

FIGS. 7 and 8 list the raw materials required and the location of each of the main components on the cassette of the present invention.

FIG. 11 is an alternate view of the cassette of the present invention.

DETAILED DESCRIPTION

[$^{18}$F]Flutemetamol may be prepared by nucleophilic substitution of a nitro group in the precursor AH111907

(6-ethoxymethoxy-2-(4'-(N-formyl-N-methyl)amino-3'-nitro)phenylbenzothiazole) by [$^{18}$F]fluoride followed by deprotection as illustrated in Scheme 1:

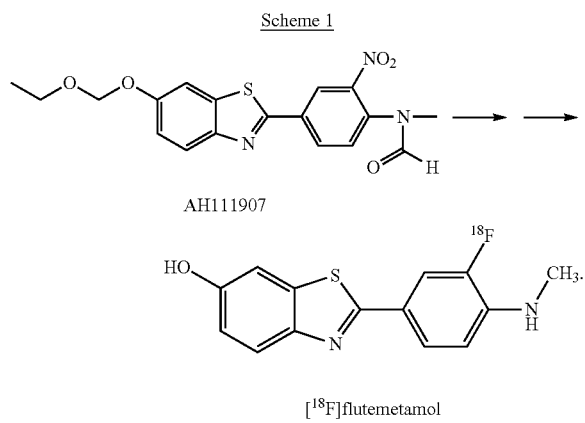

Scheme 1

AH111907

[$^{18}$F]flutemetamol

Figure 1:
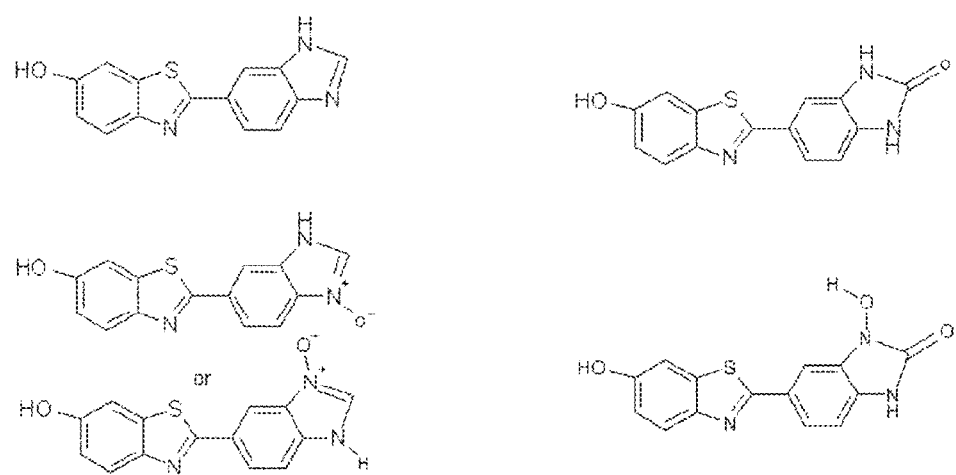
FIG. 1 depicts hydrophilic precursor derivatives.

Initial studies carried out on AH111907 (6-ethoxymethoxy-2-(4'-(N-formyl-N-methyl)amino-3'-nitro)phenylbenzothiazole) and (non-radioactive) flutemetamol demonstrated that the former reacted with strong bases to produce less lipophilic species (e.g., hydrophilic precursor derivatives of FIG. 1) while leaving the latter unaffected. Any suitable base may be used. In one embodiment, alkoxide, alkali metal hydroxides, or thiooxide bases can be used. In a further embodiment, the base is selected from the group consisting of sodium hydroxide, potassium hydroxide, sodium hydride, sodium thiomethoxide, sodium ethoxide, and sodium methoxide. In a further embodiment, the base is sodium ethoxide or sodium methoxide. In a further embodiment, the base is sodium methoxide.

In one embodiment of the invention, the "crude product reaction mixture comprising flutemetamol" of step (a) is the crude [$^{18}$F]fluoride substitution reaction mixture comprising (i) flutemetamol, (ii) the hydroxyl- and amino-protected flutemetamol having the following structure:

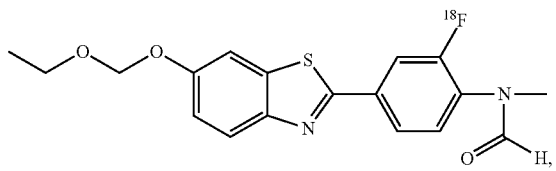

and (iii) AH111907 (6-ethoxymethoxy-2-(4'-(N-formyl-N-methyl)amino-3'-nitro)phenylbenzothiazole), each as described herein, and is treated with base at a temperature of about >100° C. followed by treatment with acid. In one embodiment of the invention, base treatment of the "crude product reaction mixture comprising flutemetamol"; preferably, the crude [$^{18}$F]fluoride substitution reaction mixture is performed at a temperature ranging between about 120-140° C.; more preferably at about 130° C. According to the invention, for the subsequent acid treatment, any mineral acid can be used. Examples of suitable acids include, but are not limited to, sulphuric acid, nitric acid, hydrochloric acid, phosphoric acid, hydrobromic acid (HBr); preferably the acid used is hydrochloric acid. The resulting less lipophilic species are then separable from [$^{18}$F]flutemetamol using solid phase extraction (SPE) cartridge.

According to the present invention, flutemetamol as used herein can be either unlabelled or radiolabeled flutemetamol. In a preferred embodiment, flutemetamol will be [$^{18}$F]flutemetamol. [$^{18}$F]flutemetamol may be prepared by any means known in the art including, but not limited to, the synthesis set forth in Scheme 1 as described herein, to give the "crude product reaction mixture comprising flutemetamol" of step (a).

The suitable source of [$^{18}$F]-fluoride ion ($^{18}$F$^-$) can be obtained as an aqueous solution from the nuclear reaction $^{18}$O (p,n)$^{18}$F and is made reactive by the addition of a cationic counterion and the subsequent removal of water. Suitable cationic counterions should possess sufficient solubility within the anhydrous reaction solvent to maintain the solubility of $^{18}$F$^-$. Therefore, counterions that have been used include large but soft metal ions such as rubidium or caesium, potassium complexed with a cryptand such as Kryptofix™, or any tetraalkylammonium salt known in the art. A preferred counterion is tetrabutyl ammonium salt. A more detailed discussion of well-known $^{18}$F labelling techniques can be found in Chapter 6 of the "Handbook of Radiopharmaceuticals" (2003; John Wiley and Sons: M. J. Welch and C. S. Redvanly, Eds.). According to the present invention, the washing step (b) removes hydrophilic compounds including the hydrophilic precursor derivatives produced during the sodium methoxide reaction (see FIG. 1) from the cartridge to waste such that flutemetamol and species of similar hydrophobicity are retained on the first reverse phase SPE cartridge. As would be understood by one of skill in the art, the specific composition of the solvent mixture will depend on the SPE cartridge used.

According to the present invention, the normal phase SPE cartridge of step (e) of a process of the invention, each as described herein, serves to retain many of the remaining hydrophilic impurities. Flutemetamol and other hydrophobic compounds pass through the normal phase SPE cartridge with minimal retention.

According to the present invention, the rinsing step (h) is performed until residual acetonitrile is present at acceptable levels for injection.

According to the invention, the eluting step (i) elutes flutemetamol and compounds of similar hydrophobicity such as residual quantities of its deprotected precursor AH111832 (6-hydroxy-2-(4'-(N-methyl)amino-3'-nitro)phenylbenzothiazole). The purified flutemetamol of step (i) is suitable for formulation.

According to the invention, the purified flutemetamol can be collected into any suitable collection vial as would be understood by one of skill in the art. A process of the present invention optionally further comprises the step of further/additional rinsing of said second reverse phase SPE cartridge with water to completely remove any flutemetamol and ethanol on the second reverse phase SPE cartridge for transfer to a collection vial, each as described herein.

Figure 9:
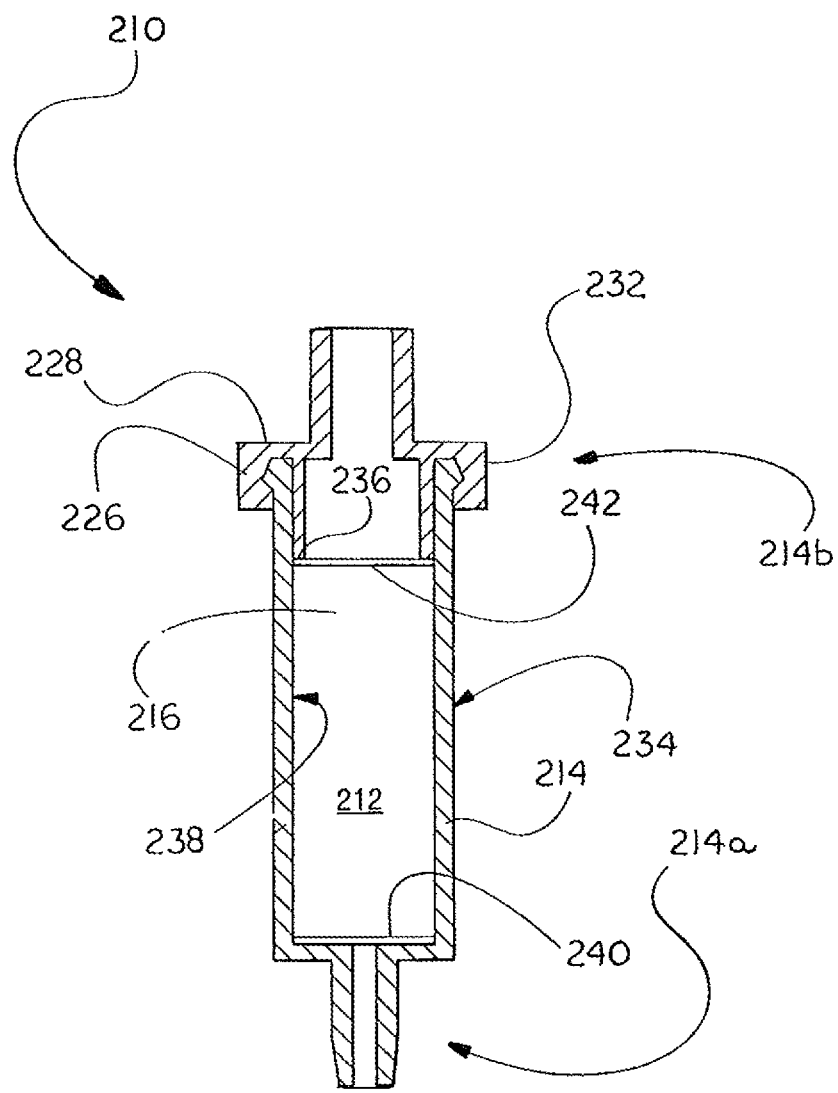
FIG. 9 depicts an SPE cartridge of the present invention.
Figure 10:
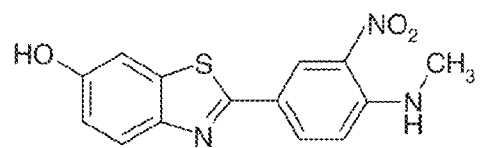
FIG. 10 depicts deprotected precursor AH111832 (6-hydroxy-2-(4'-(N-methyl)amino-3'-nitro)phenylbenzothiazole).

According to the invention, the reverse phase SPE cartridge can be any reverse phase SPE cartridge known in the art having a chain length longer than C8; preferably longer than C18; most preferably, a C30 SPE cartridge. FIG. 9 depicts an example of reverse phase SPE cartridge for use in a process of the present invention. The reverse phase SPE cartridge includes a commercially available sorbent packed between two porous media layers within an elongate cartridge body. The cartridge body includes luer fittings for simplified connection. Suitable assembled reverse phase SPE cartridges for use in the present invention can be any assembled reverse phase SPE cartridge known in the art including, but not limited to, those commercially available from Macherey-Nagel GmbH & Co. KG, Neumann-Neander-Strasse 6-8, D-52355 Dueren, Germany. Suitable sorbents for use in a reverse phase SPE cartridge can be any sorbent know in the art including, but not limited to those, commercially available from Princeton Chromatography Inc., Cranbury, N.J. 08512 USA. An example of suitable sorbent is a C30 sorbent. According to the invention, a C30 cartridge is preferred as it provides higher retention capability compared to shorter-chain reverse phase cartridges (C8, C18) and can be used for the separation of flutemetamol from its hydrophilic precursor derivatives.

Primary Purification—Reverse Phase SPE

In one embodiment of the invention, the first reverse phase SPE cartridge may be a reverse phase SPE cartridge as described herein. In a preferred embodiment of the invention the first reverse phase SPE cartridge is a C30 cartridge.

In one embodiment of the invention, the first reverse phase SPE cartridge may optionally be conditioned with acetonitrile followed by water prior to step (a) as described above.

In one embodiment of the invention, after step (b), the first reverse phase SPE cartridge may optionally be flushed with nitrogen and/or vacuum.

In one embodiment of the invention, in step (b) the sorbent of the first reverse phase SPE cartridge is washed with 40% acetonitrile:60% water (v/v) and then the first reverse phase SPE cartridge is flushed with nitrogen and/or vacuum.

In one embodiment of the invention, in step (b) the sorbent of the first reverse phase SPE cartridge is washed with water and then the first reverse phase SPE cartridge is flushed with nitrogen and/or vacuum.

In one embodiment of the invention, in step (d) flutemetamol is eluted from the first reverse phase SPE cartridge with 35-45% acetonitrile:water (v/v).

Figure 2:
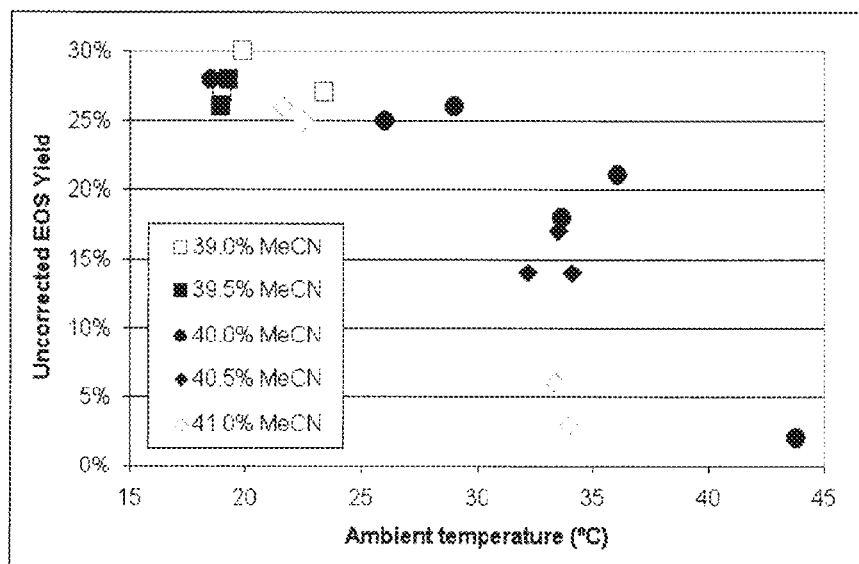
FIG. 2 depicts the effect of ambient temperature and acetonitrile concentration on yield.
Figure 3:
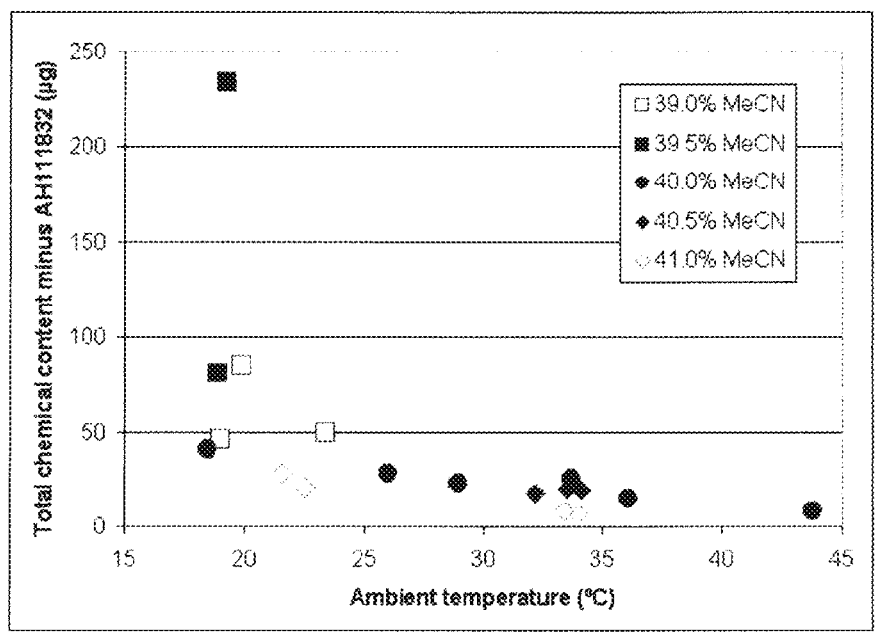
FIG. 3 depicts the effect of ambient temperature and acetonitrile concentration on level of chemical impurities.

In an embodiment of the invention, acceptable yield and purity is obtained by performing these steps in the first reverse phase SPE cartridge at a temperature between about 19° C. and about 34° C.; preferably between about 20° C.-30° C. (i.e., the hot cell ambient temperature in which the first reverse phase SPE cartridge is located) and using an acetonitrile/water mixture where the water concentration is about 35-45% of the total (v/v) (e.g., 40% water+60% acetonitrile); preferably, about 39.5-40.5% of the total (v/v). (See FIGS. 2 and 3). At lower temperatures and lower concentrations of acetonitrile, flutemetamol-related compounds are bound more tightly to the solid phase and are therefore less susceptible to being lost to waste during the acetonitrile/water washing. The result is a high yield of flutemetamol but with a greater level of impurities. The opposite effect is seen at higher temperatures and higher concentrations of acetonitrile. This combination gives higher purity but much lower yield.

Secondary Purification—Normal Phase SPE

According to the invention, the normal phase SPE cartridge can be any normal phase SPE cartridge known in the art. Examples of suitable normal phase SPE cartridges include, but are not limited to, amino, cyano, diol, alumina, and silica normal phase SPE cartridges.

In one embodiment of the invention, a normal phase SPE cartridge will contain normal phase materials such as silica-based amino stationary phase to selectively trap hydrophilic impurities from an acetonitrile solution without also retaining flutemetamol. Any silica-based amino stationary phase (i.e., amino sorbent) known in the art can be used. Examples of suitable "silica-based amino stationary phase" include, but are not limited to, those commercially available from Waters (Milford, Mass., USA). In one embodiment of the invention, during the FASTlab™ process, as described herein, amino cartridges, or normal phase SPE cartridges, (e.g., Varian Bond Elut Jr $NH_2$ cartridge) can be used on FASTlab™.

In one embodiment of the invention, the amino sorbent of the normal phase SPE cartridge of step (e) is first conditioned by passing acetonitrile through the normal phase SPE cartridge and then drying the cartridge under a flow of nitrogen, prior to the flutemetamol/acetonitrile fraction from the first reverse phase SPE cartridge being passed through it. According to the present invention, the normal phase SPE cartridge of step (e) may optionally be further rinsed with acetonitrile in order to maximise flutemetamol recovery prior to step (f).

In one embodiment of the invention, the amino sorbent is first conditioned by passing acetonitrile through the normal phase SPE cartridge and then dried under a flow of nitrogen. The flutemetamol/acetonitrile fraction from the first reverse phase SPE cartridge is passed through the amino cartridge and into a FASTlab™ syringe. The amino cartridge is then rinsed with a further acetonitrile to maximise flutemetamol recovery.

Solvent Exchange—Second Reverse Phase SPE

After the secondary purification by means of the normal phase SPE cartridge, acetonitrile (and any residual methanol) may be removed before the purified drug substance (i.e. flutemetamol) is transferred to the product collection vial. This can be achieved by performing solvent exchange on a second reverse phase SPE cartridge. According to the present invention, the second reverse phase SPE cartridge may be a reverse phase SPE cartridge as described herein. In a preferred embodiment of the invention, the second reverse phase SPE cartridge is a C30 cartridge.

In one embodiment of the invention, the second reverse phase SPE cartridge can optionally be pre-conditioned with acetonitrile and water.

In one embodiment of the invention, prior to passing through the second reverse phase SPE cartridge, the acetonitrile/flutemetamol product solution from the normal phase SPE/amino cartridge is diluted with water such that the loading solution is below about 50% acetonitrile in order to trap flutemetamol onto the sorbent of the second reverse phase SPE cartridge.

In one embodiment of the invention, the second reverse phase SPE cartridge is subsequently rinsed with water to remove residual solvents, before the flutemetamol is eluted from the cartridge into a product collection vial using first ethanol then water.

A purification process of the invention can be performed manually. A purification process of the invention can be automated. In a preferred embodiment, a purification process of the invention is performed on an automated system/platform.

In a preferred embodiment, a process of the present invention is automated. [$^{18}$F]flutemetamol may be conveniently prepared in an automated fashion by means of an automated radiosynthesis apparatus. There are several commercially-available examples of such apparatus, including TRACERlab™ and FASTlab™ (both commercially available from GE Healthcare a division of General Electric Company). In a preferred embodiment of the invention, the automated radiosynthesis apparatus is FASTlab™. Automated radiosynthesis apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

The present invention therefore provides in another aspect of the present invention, a cassette for the automated synthesis and purification of [$^{18}$F]flutemetamol each as defined herein comprising:
(i) a vessel containing crude product reaction mixture comprising flutemetamol;
(ii) a first reverse phase SPE cartridge;
(iii) means for washing and eluting the first reverse phase SPE cartridge;
(iv) a normal phase SPE cartridge;
(v) a second reverse phase SPE cartridge; and
(vi) means for rinsing and eluting the second reverse phase SPE cartridge;
wherein each component is as described herein.

Advantages to such an on-cassette SPE cartridge-based process includes reduction of overall synthesis time and cost as well as improved process reproducibility.

Reference is now made to FIGS. 5-9 and 11, which depict a disposable synthesis cassette 110 and its components which are useful for performing the method of the present invention. FIG. 6 depicts the numbering of each position 1-25 of the cassette manifold of the present invention, each position also referring to the manifold valve of manifold 112. FIG. 7 lists the raw materials required for the cassette of the present invention. FIG. 8 lists the location of each of the main components on the cassette of the present invention.

Cassette 110 includes, a manifold 112 including twenty-five 3 way/3 position stopcocks valves 1-25, respectively. Manifold valves 1-25 are also referred to as their manifold positions 1-25 respectively. Manifold valves 1, 4-5, 7-10, 17-23, and 25 have female luer connectors projecting up therefrom. Valves 2, 6, and 12-16 have an elongate open vial housing upstanding therefrom and support an upstanding cannula therein for piercing a reagent vial inserted in the respective vial housing. Movement of the reagent vial to be pierced by the respective cannula is performed under actuation by the synthesizer device. Valves 3, 11, and 24 support an elongate open syringe barrel upstanding therefrom. Valves 1-25 include three open ports opening to adjacent manifold valves and to their respective luer connectors, cannulas, and syringe barrels. Each valve includes a rotatable stopcock which puts any two of the three associated ports in fluid communication with each other while fluidically isolating the third port. Manifold 112 further includes, at opposing ends thereof, first and second socket connectors 121 and 123, each defining ports 121a and 123a, respectively. Manifold 112 and the stopcocks of valves 1-25 are desirably formed from a polymeric material, e.g. PP, PE, Polysulfone, Ultem, or Peek.

Cassette 110 is a variant of a pre-assembled cartridge designed to be adaptable for synthesizing clinical batches of different radiopharmaceuticals with minimal customer installation and connections. Cassette 110 includes reaction vessel, reagent vials, cartridges, filters, syringes, tubings, and connectors for synthesizing a radiotracer according to the present invention. Connections are desirably automatically made to the reagent vials by driving the septums thereof onto penetrating spikes to allow the synthesizer access to use the reagents.

Cassette 110 is attachable to a synthesis device, such as FASTLab, which cooperatively engages the cassette so as to be able to actuate each of the stopcocks and syringes to drive a source fluid with a radioisotope through the cassette for performance of a chemical synthesis process. Additionally, the synthesis device can provide heat to the reaction vessel of cassette 110 as required for chemical reactions. The synthesizer is programmed to operate pumps, syringes, valves, heating element, and controls the provision of nitrogen and application of vacuum to the cassette so as to direct the source fluid into mixing with the reagents, performing the chemical reactions, through the appropriate purification cartridges, and selectively pumping the output tracer and waste fluids into appropriate vial receptacles outside the cassette. The fluid collected in the output vial is typically input into another system for either purification and/or dispensement. After product dispensement, the internal components of cassette 110 are typically flushed to remove latent radioactivity from the cassette, although some activity will remain. Cassette 110 thus can be operated to perform a two-step radiosynthesis process. By incorporating SPE cartridges on the manifold, cassette 110 is further able to provide simple purification so as to obviate the need for HPLC.

Figure 5:
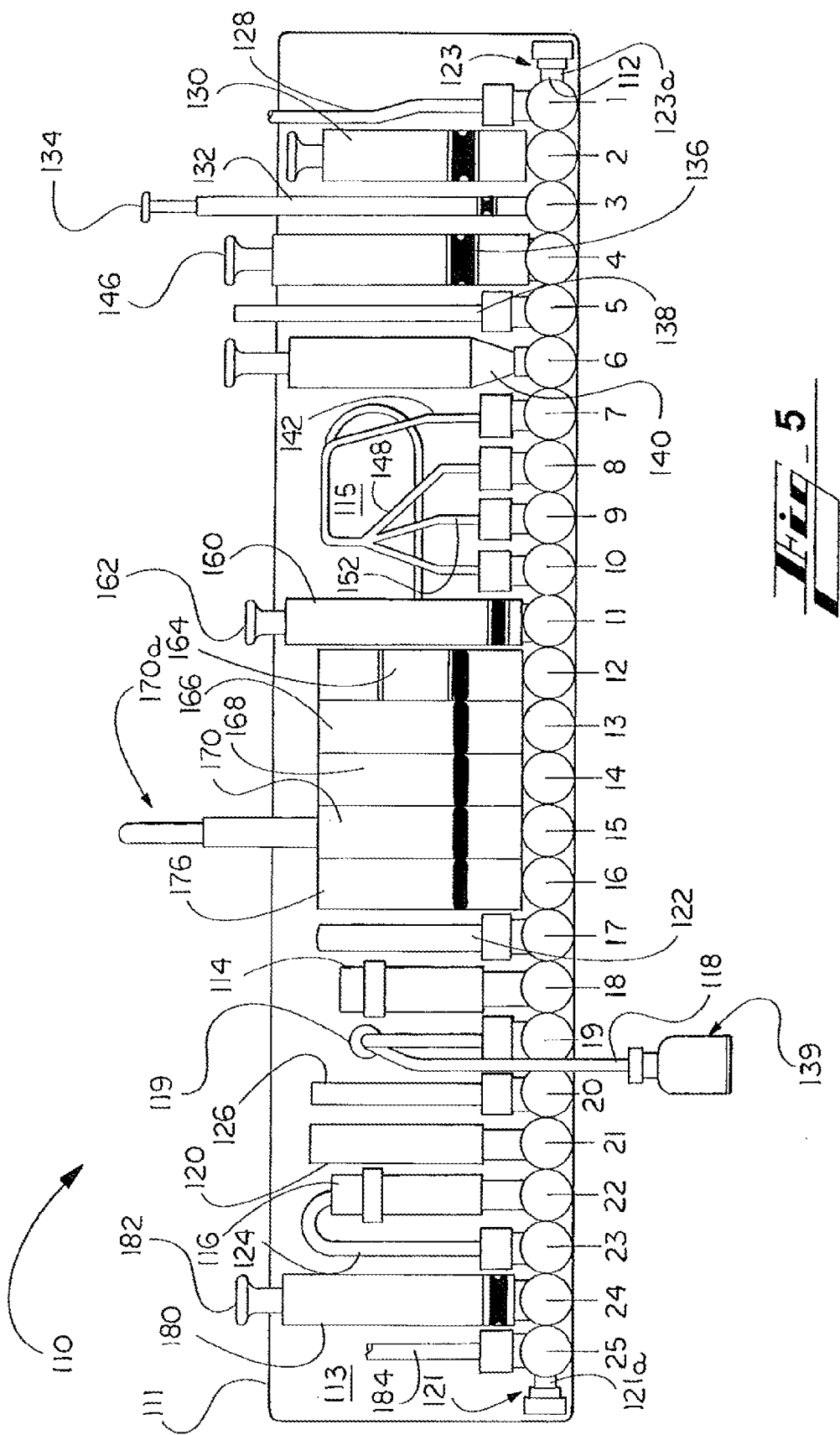
FIG. 5 is a picture of a fully assembled cassette of the present invention for the production of Flutemetamol ($^{18}$F) Injection, showing all tubing and prefilled reagent vials and the SPE cartridge.

FIGS. 5 and 11 depicts a fully assembled cassette 110 of the present invention for the production of Flutemetamol ($^{18}$F) Injection, showing all tubing and prefilled reagent vials. Cassette 110 includes a polymeric housing 111 having a planar major front surface 113 and defining a housing cavity 115 in which manifold 112 is supported. A first reverse phase SPE Cartridge 114 is positioned at manifold position 18 while a second reverse phase SPE cartridge 116 is positioned at manifold position 22. A normal phase (or amino) SPE cartridge 120 is located at manifold position 21. First SPE Cartridge 114 is used for primary purification. The amino cartridge 120 is used for secondary purification. The second SPE Cartridge 116 is used for solvent exchange. A 50 cm to over-2 m length of Tygon tubing 118 is connected between cassette position 19 and a product collection vial 129 in which occurs the formulation of the drug substance. Tubing 118 is shown in partial phantom line to indicate where is passing behing front surface 113 on the far side of manifold 112 in the view. While some of the tubings of the cassette are, or will be, indentified as being made from a specific material, the present invention contemplates that the tubings employed in cassette 110 may be formed from any suitable polymer and may be of any length as required. Surface 113 of housing 111 defines an aperture 119 through which tubing 118 transits between valve 19 and the product collection vial 139. FIG. 11 depicts the same assembled manifold of the cassette and shows the connections to a vial containing a mixture of 40% MeCN and 60% water at manifold position 9, a vial of 100% MeCN at manifold position 10, a water vial connected at the spike of manifold position 14, and a product collection vial connected at manifold position 19. FIG. 11 depicts manifold 112 from the opposite face, such that the rotatable stopcocks and the ports 121a and 123a are hidden from view.

A 14 cm length of a tubing 122 extends between the free end of cartridge 114 and the luer connector of manifold valve 17. An 8 cm length of tubing 124 extends between the free end of cartridge 116 and the luer connector of manifold valve 23. A 14 cm length of tubing 126 extends between the free end of cartridge 120 and the luer connector of manifold valve 20. Additionally, tubing 128 extends from the luer connector of manifold valve 1 to a target recovery vessel 129 (shown in FIG. 11) which recovers the waste enriched water after the fluoride has been removed by the QMA cartridge. The free end of tubing 128 supports a connector 131, such as a luer fitting or an elongate needle and associated tubing, for connecting the cavity to the target recovery vessel 129. In the method of the present invention, the radioisotope is [$^{18}$F] fluoride provided in solution with H$_2$[$^{18}$O] target water and is introduced at manifold valve 6.

A tetrabutylammonium bicarbonate eluent vial 130 is positioned within the vial housing at manifold valve 2 and is to be impaled on the spike therein. An elongate 1 mL syringe pump 132 is positioned at manifold valve 3. Syringe pump 132 includes an elongate piston rod 134 which is reciprocally moveable by the synthesis device to draw and pump fluid through manifold 112 and the attached components. QMA cartridge 136 is supported on the luer connector of manifold valve 4 and is connected via a 14 cm length of silicone tubing 138 to the luer connector of manifold position 5. Cartridge 136 is desirably a QMA light carbonate cartridge sold by Waters, a division of Millipore. The tetrabutylammonium bicarbonate in an 80% acetonitrile; 20% water (v/v) solution provides elution of [$^{18}$F]fluoride from QMA and phase transfer catalyst. A fluoride inlet reservoir 140 is supported at manifold valve 6.

Manifold valve 7 supports a tubing 142 at its luer connector which extends to a first port 144 of a reaction vessel 146. The luer connector of manifold valve 8 is connected via a 14 cm length of tubing 148 to a second port 150 of reaction vessel 146. The luer connector of manifold valve 9 is connected via a 42 cm length of tubing 152 to a vial 154 containing a mixture of 40% MeCN and 60% water (v/v). The acetonitrile and water mixture is used to enable primary purification of flutemetamol at the first SPE cartridge 114. The luer connector of manifold valve 10 is connected via a 42 cm length of tubing 156 to a vial 158 containing 100% MeCN used for conditioning of the cartridges and the elution of flutametamol from the first SPE cartridge 114. Manifold valve 11 supports a barrel wall for a 5 ml syringe pump 160. Syringe pump 160 includes an elongate piston rod 162 which is reciprocally moveable by the synthesis device so as to draw and pump fluid through manifold 112. The vial housing at manifold valve 12 receives vial 164 containing 6-ethoxymethoxy-2-(4'-(N-formyl-N-methyl)amino-3'-nitro)phenylbenzothiazole). The vial housing at manifold valve 13 receives a vial 166 containing 4M hydrochloric acid. The hydrochloric acid provides deprotection of the radiolabelled intermediate. The vial housing at manifold valve 14 receives a vial 168 of a methanol solution of sodium methoxide. The vial housing at manifold valve 15 receives an elongate hollow spike extension 170 which is positioned over the cannula at manifold valve 15 and provides an elongate water bag spike 170a at the free end thereof. Spike 170 pierces a cap 172 of a water bottle 174 containing water for both diluting and rinsing the fluid flowpaths of cassette 110. The vial housing at manifold valve 16 receives a vial 176 containing ethanol. Ethanol is used for the elution of the drug substance from the second SPE cartridge 116. The luer connector of manifold valve 17 is connected to a 14 cm length of silicone tubing 122 to SPE cartridge 114 at position 18. Manifold valve 24 supports the elongate barrel of a 5 ml syringe pump 180. Syringe pump 180 includes an elongate syringe rod 182 which is reciprocally moveable by the synthesis device to draw and pump fluid through manifold 112 and the attached components. The luer connector of manifold valve 25 is connected to a 42 cm length of a tubing 184 to a third port 186 of reactor vessel 146.

Cassette 110 is mated to an automated synthesizer having rotatable arms which engage each of the stopcocks of valves 1-25 and can position each in a desired orientation throughout cassette operation. The synthesizer also includes a pair of spigots, one of each of which insert into ports 121a and 123a of connectors 121 and 123 in fluid-tight connection. The two spigots respectively provide a source of nitrogen and a vacuum to manifold 112 so as to assist in fluid transfer therethrough and to operate cassette 110 in accordance with the present invention. The free ends of the syringe plungers are engaged by cooperating members from the synthesizer, which will then apply the reciprocating motion thereto within the syringes. A bottle containing water is fitted to the synthesizer then pressed onto spike 170 to provide access to a fluid for driving compounds under operation of the various-included syringes. The reaction vessel will be placed within the reaction well of the synthesizer and the product collection vial and waste vial are connected. The synthesizer includes a radioisotope delivery conduit which extends from a source of the radioisotope, typically either vial or the output line from a cyclotron, to a delivery plunger. The delivery plunger is moveable by the synthesizer from a first raised position allowing the cassette to be attached to the synthesizer, to a second lowered position where the plunger is inserted into the housing at manifold valve 6. The plunger provides sealed engagement with the housing at manifold valve 6 so that the vacuum applied by the synthesizer to manifold 112 will draw the radioisotope through the radioisotope delivery conduit and into manifold 112 for processing. Additionally, prior to beginning the synthesis process, arms from the synthesizer will press the reagent vials onto the cannulas of manifold 112. The synthesis process may then commence.

FIG. 9 depicts an SPE cartridge 210 of the present invention. The sorbent fill 212 of the reverse phase SPE cartridges will differ from the fill of the normal phase SPE cartridge. Cartridge 210 includes an elongate tubular body 214 defining a cylindrical cavity 216. A first end 214a of body 214 includes a transverse annular wall 218 defining a exit aperture 220 in fluid communication with cavity 216. Annular wall 218 also supports an elongate open tubular wall 222 forming a luer tip 224. The opposing second end 214b of body 214 supports an end cap 226 having a cap body 228 defining an inlet aperture 230 in fluid communication with cavity 216. Cap body 228 includes an outer annular rim 232 engaging the outer surface 234 of tubular body 214 at second end 214b and an inner annular wall 236 engaging the inner surface 238 of tubular body 214 at second end 214b. Cartridge 210 also includes circular disc-shaped porous filter elements 240 and 242 spanning across cavity 216 with sorbent fill 212 therebetween. By way of illustration and not of limitation, cartridge 210 is generally about 48.6 mm in length, about 15.2 mm in diameter at second end 214b, about 12.0 mm in diameter at first end 214a and cavity 216 is about 34.6 mm in length, although the size and shape of cartridge 210 may be selected as will be suitable for its intended purpose.

EXAMPLES

Example 1

FASTlab™ Synthesis of [$^{18}$F]flutemetamol Injection Using SPE Purification

Figure 4:
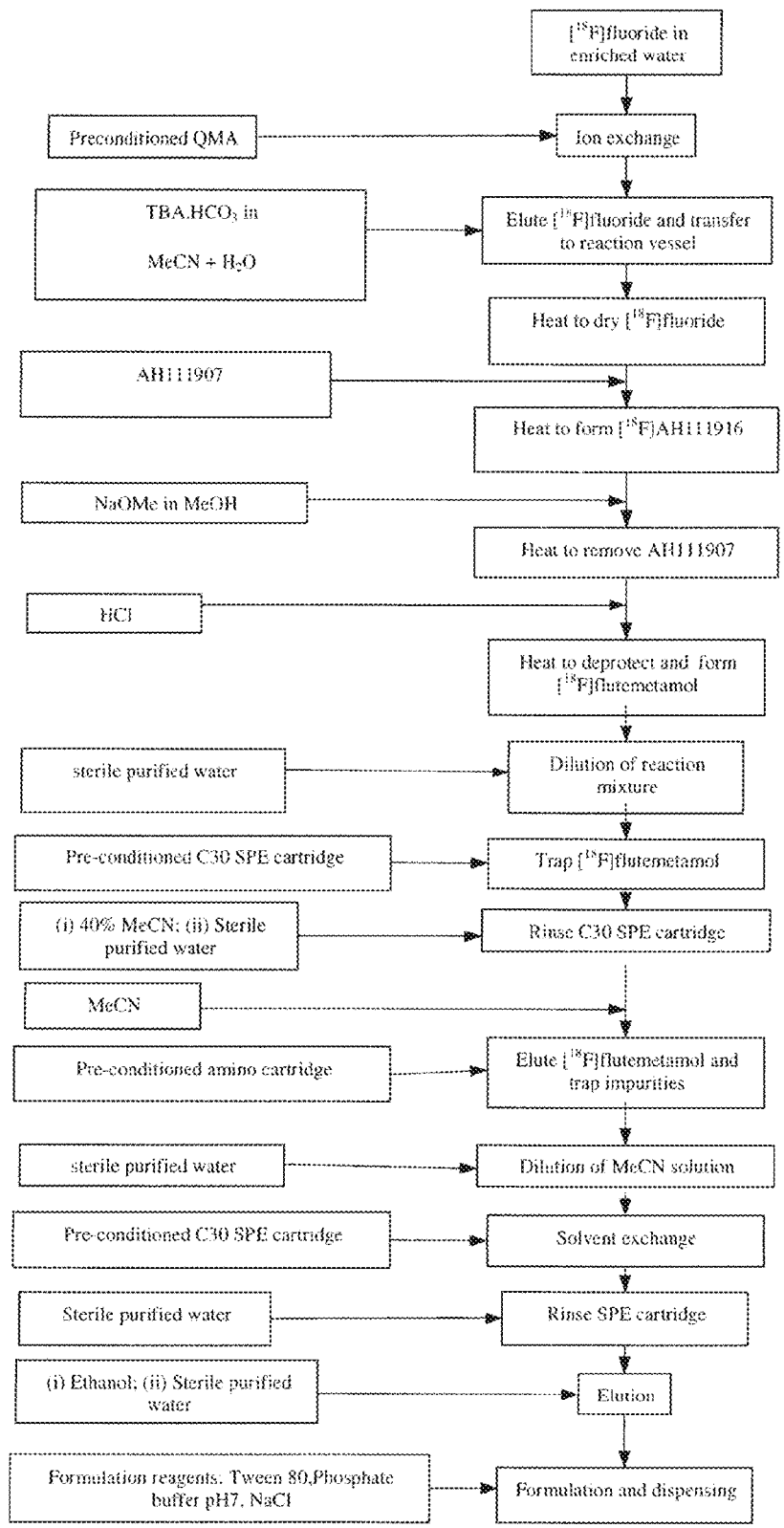
FIG. 4 depicts a flow chart describing the production and formulation of Flutemetamol ($^{18}$F) Injection on a cassette of the present invention.

With reference to FIGS. 4, 7 and 8, the production and formulation of Flutemetamol ($^{18}$F) Injection on a cassette of the present invention is described. For this process, the cassette of FIGS. 5 and 11 was constructed for operation by the FASTlab™ machine. First, [$^{18}$F]fluoride solution is transferred by vacuum to the FASTlab™ and is trapped on a QMA cartridge (commercially available from Waters (Milford, Mass. USA)) that had been preconditioned. The [$^{18}$O]enriched water is recovered and takes no further part in the synthesis. The [$^{18}$F]fluoride is then eluted directly from the QMA cartridge into the reaction vessel with tetrabutylammonium bicarbonate solution (350 µl, 0.15 M in 80:20 acetonitrile:water).

The reaction vessel is heated by the synthesis unit under a flow of nitrogen and a vacuum in order to dry the [$^{18}$F]fluoride and remove the QMA eluent solvents. For the radiolabelling reaction, the final intermediate, AH111907 (6-ethoxymethoxy-2-(4'-(N-formyl-N-methyl)amino-3'-nitro)phenylbenzothiazole) in anhydrous dimethyl sulfoxide (DMSO) is added to the reaction vessel. The vessel is subsequently sealed, by positioning manifold valves 7, 8, and 25 to seal the vessel, and heated. Sodium methoxide in methanol is added to the reaction vessel, which is then heated. To effect deprotection, hydrochloric acid is added to the reaction vessel, which is then heated. The crude deprotected reaction mixture containing [$^{18}$F]flutemetamol is diluted with sterile purified water (about 2 ml) before being passed through the first reverse phase SPE cartridge 114.

For the primary SPE purification, the first reverse phase SPE cartridge 114 is washed with 12 ml 40% acetonitrile: 60% water (v/v), followed by 5 ml water in order to remove the majority of the impurities (including the hydrophilic precursor derivatives). The partially purified flutemetamol is eluted from the first reverse phase SPE cartridge 114 in 2 ml acetonitrile.

For the secondary SPE purification, the normal phase, the 2 ml acetonitrile solution from the first reverse phase SPE cartridge is passed back and forth through the amino cartridge (or normal phase SPE cartridge) 120 in order to trap many of the remaining hydrophilic impurities. The amino cartridge is then rinsed with a further 1 ml acetonitrile to maximise recovery of flutemetamol.

For then performing solvent exchange and formulation, the acetonitrile solution (about 3 mL) from the amino cartridge 120 is diluted with water (about 5.5 mL) and passed through the second C30 cartridge 116. The C30 cartridge 116 is then rinsed three times with water (up to about 20 mL in total) to reduce levels of acetonitrile and methanol. The drug substance [$^{18}$F]flutemetamol is retained on the cartridge 116 and eluted with ethanol (about 3.5 ml) into the product collection vial prefilled with polysorbate 80, phosphate buffer and sodium chloride to give Flutemetamol [$^{18}$F] Injection. The C30 cartridge 116 is further eluted with water (about 9.3 mL) in order to flush out any remaining ethanol and this passes directly into the product collection vial. One of the FASTlab™ syringes then draws the contents of the product collection vial up and down in order to homogenise the drug product.

All patents, journal articles, publications and other documents discussed and/or cited above are hereby incorporated by reference.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

The invention claimed is:

1. A cassette for use in an automated radiosynthesis apparatus comprising:
   (i) a vessel containing a crude product reaction mixture comprising [18F]flutemetamol;
   (ii) a first reverse phase solid phase extraction (SPE) cartridge;
   (iii) means for washing and eluting said first reverse phase SPE cartridge;
   (iv) a normal phase SPE cartridge;
   (v) a second reverse phase SPE cartridge; and
   (vi) means for rinsing and eluting said second reverse phase SPE cartridge.

2. The cassette according to claim 1 wherein said first reverse phase SPE cartridge and said second reverse phase SPE cartridge are each a C30 SPE cartridge.

3. The cassette according to claim 2 wherein said first reverse phase SPE cartridge and said second reverse phase SPE cartridge are each pre-conditioned with acetonitrile and water.

* * * * *